US012636461B2

(12) United States Patent
Lacey et al.

(10) Patent No.: US 12,636,461 B2
(45) Date of Patent: May 26, 2026

(54) ELECTRONIC VAPORIZER SYSTEM AND METHOD OF CONTROLLING THE SAME

(71) Applicant: GE Precision Healthcare LLC, Wauwatosa, WI (US)

(72) Inventors: Joseph J. Lacey, Madison, WI (US); Russell J. Kuzelka, Madison, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 1382 days.

(21) Appl. No.: 17/347,252

(22) Filed: Jun. 14, 2021

(65) Prior Publication Data

US 2022/0395665 A1 Dec. 15, 2022

(51) Int. Cl.
*A61M 16/18* (2006.01)
*A61M 16/00* (2006.01)
*A61M 16/10* (2006.01)

(52) U.S. Cl.
CPC ........ *A61M 16/18* (2013.01); *A61M 16/0003* (2014.02); *A61M 16/026* (2017.08);
(Continued)

(58) Field of Classification Search
CPC .............. A61M 16/18; A61M 16/0003; A61M 16/026; A61M 16/1005; A61M 2016/0036; A61M 2016/1035; A61M 2205/502; A61M 16/01; A61M 16/024; A61M 16/0891; A61M 16/1015; A61M 16/104; A61M 16/0051; A61M 16/12; A61M 2202/0241; A61M 2205/3327; A61M 2205/50; A61M 2230/005; A61M 2230/437; A61B 5/082; A61B 5/0833; A61B 5/0836; A61B 5/0022; A61B 5/087; A61B 5/291; A61B 5/369; A61B 5/4821; A61B 5/4839;
(Continued)

(56) References Cited

U.S. PATENT DOCUMENTS 6,131,571 A * 10/2000 Lampotang ....... A61M 16/0069
128/204.23
RE41,291 E 4/2010 Viertio-Oja et al.
(Continued)

FOREIGN PATENT DOCUMENTS

WO 2006094172 A2 9/2006
WO WO-2013142973 A1 * 10/2013 ............ A61M 16/01

OTHER PUBLICATIONS

EP patent application 22177503.4 filed Jun. 7, 2022—extended Search Report issued Nov. 11, 2022; 7 pages.

Primary Examiner — Valerie L Woodward
(74) Attorney, Agent, or Firm — Andrus Intellectual Property Law, LLP

(57) ABSTRACT

An electronic vaporizer system includes an anesthetic sump containing anesthetic agent, a vaporizer unit that vaporizes the anesthetic agent from the sump and delivers the vaporized agent to a patient breathing circuit, and a gas sensor configured to measure end tidal concentration of the anesthetic agent and exhalation gasses from the patient. A control system is configured to receive the measured end tidal concentration of anesthetic agent and compare the measured end tidal concentration to a desired end tidal concentration to be maintained for the patient. The vaporizer unit is then automatically controlled to deliver an amount of vaporized agent to the patient based on the comparison.

21 Claims, 5 Drawing Sheets

(52) U.S. Cl.
CPC . *A61M 16/1005* (2014.02); *A61M 2016/0036*
(2013.01); *A61M 2016/1035* (2013.01); *A61M*
*2205/502* (2013.01)

(58) Field of Classification Search
CPC ....... A61B 5/6814; A61B 5/746; A61B 5/083;
A61B 5/256; A61B 5/386; A61B 5/72;
A61B 2560/0443; A61B 2562/221; G16H
20/40; G16H 40/63
See application file for complete search history.

(56) References Cited

U.S. PATENT DOCUMENTS

| | | | |
|---|---|---|---|
| 11,167,084 B2 * | 11/2021 | Guerrini | ............. A61M 5/1723 |
| 2006/0196505 A1 | 9/2006 | Izuchukwu | |
| 2010/0212666 A1 | 8/2010 | Bouillon et al. | |
| 2011/0056491 A1 * | 3/2011 | Rumph | ............... A61M 16/209 |
| | | | 128/203.14 |
| 2012/0285450 A1 * | 11/2012 | Wang | ..................... G16H 10/65 |
| | | | 128/203.14 |
| 2014/0130801 A1 * | 5/2014 | Cipolli | .................. A61M 16/12 |
| | | | 128/203.25 |
| 2014/0352693 A1 * | 12/2014 | Pessala | ............. A61M 16/0051 |
| | | | 128/203.14 |
| 2015/0059744 A1 | 3/2015 | Fisher | |
| 2018/0296759 A1 | 10/2018 | Dumont et al. | |
| 2019/0374158 A1 | 12/2019 | Brown et al. | |

* cited by examiner

ELECTRONIC VAPORIZER SYSTEM AND METHOD OF CONTROLLING THE SAME

BACKGROUND

The present disclosure generally relates to anesthesia delivery systems, and more particularly to vaporizer systems that deliver vaporized anesthetic agent to a patient's breathing circuit.

Anesthetic agents induce a hypnotic state in a patient by the administration of such a drug, such as via inhalation of the drug through the patient's breathing circuit. Typical inhaled anesthetic agents include Sevoflurane, Isoflurane, Desflurane, and Enflurane, among others. These inhalation anesthetic agents are generally stored as a liquid and then vaporized in a vaporizer system. The vaporized anesthetic agent is mixed into the fresh gas and other ventilation gases delivered to the patient. Various types of anesthetic vaporizers are well known in the relevant art, including plenum vaporizers, drawover vaporizers, and dual-circuit gas-vapor blenders.

The anesthetic agent acts on the brain to produce a lessening or loss of consciousness in the patient. The extent to which the patient is anesthetized is often termed the "depth of anesthesia" or "hypnotic level." Various patient monitoring devices are available for measuring a patient's depth of anesthesia, such as a bispectral index (BIS) monitor which analyzes the complexity of electroencephalographic (EEG) data obtained from the patient as a sensed indication of the hypnotic level of the patient. Other depth of anesthesia monitoring methods and systems are known, including train-of-four monitors, facial twitch monitors, and others.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one embodiment, an electronic vaporizer system includes an anesthetic sump containing anesthetic agent, a vaporizer unit that vaporizes the anesthetic agent from the sump and delivers the vaporized agent to a patient breathing circuit, and a gas sensor configured to measure end tidal concentration of the anesthetic agent and exhalation gasses from the patient. A control system is configured to receive the measured end tidal concentration of anesthetic agent and compare the measured end tidal concentration to a desired end tidal concentration to be maintained for the patient. The vaporizer unit then automatically controls the delivery of a controlled amount of vaporized agent to the patient based on the comparison.

In one embodiment, a method of controlling a vaporizer system configured to vaporize an anesthetic agent and deliver the vaporized agent to a patient breathing circuit includes measuring end tidal concentration of the anesthetic agent in exhalation gasses from the patient and comparing the measured end tidal concentration to a desired end tidal concentration to be maintained for the patient. The vaporizer unit is then automatically controlled to deliver an amount of vaporized agent to the patient breathing circuit based on the comparison so as to maintain the measured end tidal concentration within a predetermined range of the desired end tidal concentration.

Various other features, objects, and advantages of the invention will be made apparent from the following description taken together with the drawings.

BRIEF DESCRIPTION OF THE DRAWINGS

The present disclosure is described with reference to the following Figures.

DETAILED DESCRIPTION

Figure 1:
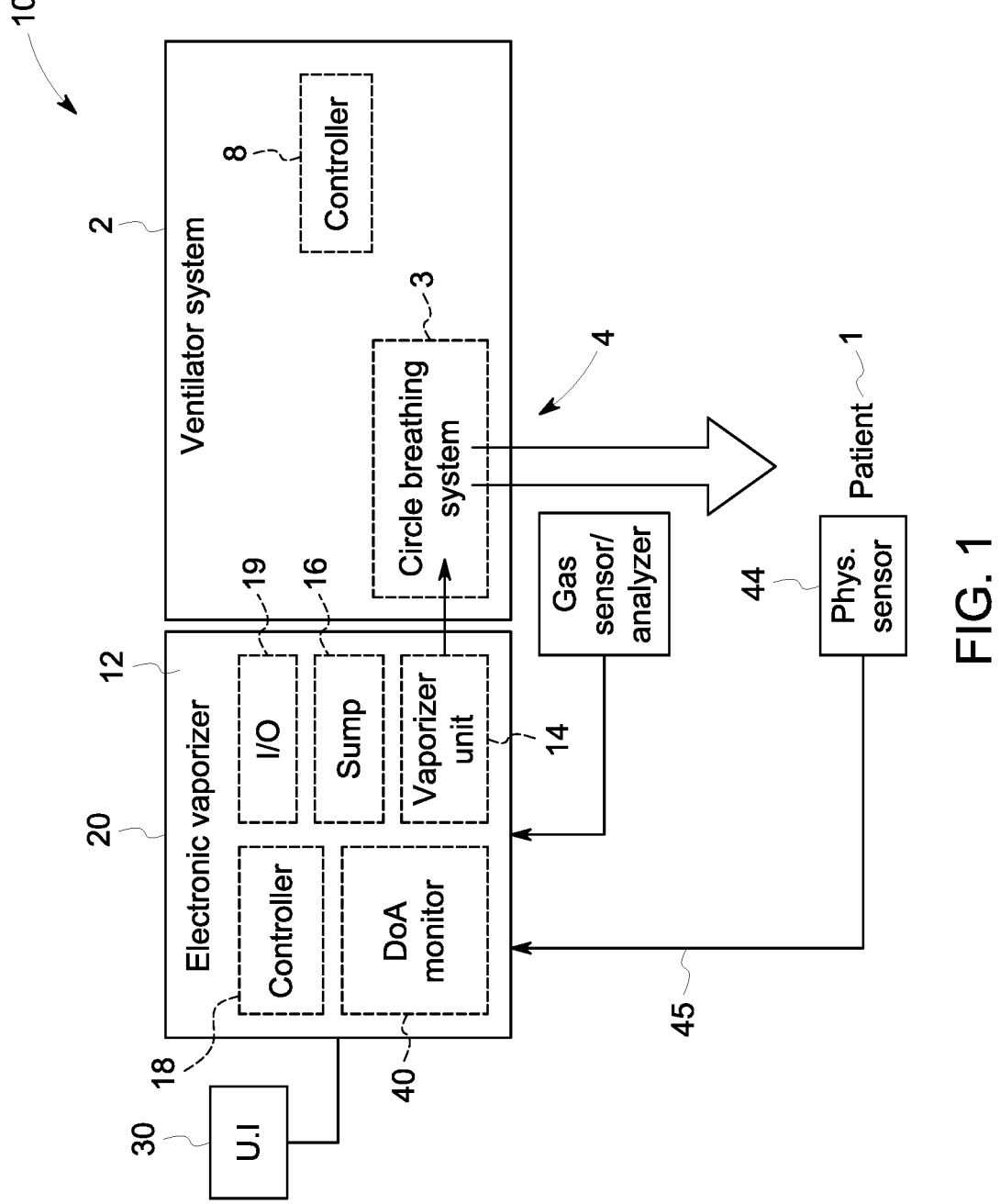
FIG. 1 depicts one embodiment of an electronic vaporizer system connected to a ventilator system for delivering anesthesia to a patient.

As described above, vaporizers take liquid anesthetic agent, such as Sevoflurane or Desflurane, and convert it to a vapor that gets titrated out to the patient. The patient inhales the anesthetic vapor with the breathing gasses delivered by the ventilator. Mechanically controlled vaporizer systems are a very common type of vaporizer system worldwide. Mechanical vaporizers are open-loop-control systems where a clinician sets a delivery amount for the vaporizer, such as by controlling a dial on the housing of the vaporizer system. Depending on the needs of the patient and the needed depth of anesthesia, or hypnotic level, based on the medical care being provided to the patient, the clinician manually adjusts the delivery amount of agent provided by the manual vaporizer.

The present inventors have recognized problems with manual vaporizers, which require significant attention and resources by the clinician to properly operate them to deliver optimal anesthetic amounts to the patient. Further, open-loop-controlled systems are subject to human error, where busy clinicians with divided attention may not provide optimal ventilator control settings and timing, and thus a patient may receive too little or too much anesthesia at any given point in a medical procedure. Yet, the inventors have also recognized that many care facilities may be unable to purchase entirely new anesthesia delivery and ventilator systems providing closed-loop-control.

Further, the inventors have recognized that controlling anesthesia delivery based on end tidal concentration of the anesthetic agent in the exhalation gasses from the patient would provide an effective close-loop-control means, and that such closed-loop-control is desirable and overcomes issues relating to human capital and clinician error.

In view of the foregoing challenges in the relevant art recognized by the inventors, the inventors have developed the disclosed electronic vaporizer system which can be retrofitted into current ventilator systems providing anesthesia delivery capabilities, such as having a circle breathing system. The disclosed electronic vaporizer systems replace mechanical vaporizers in existing anesthesia systems, and thus are configured to connect into the breathing circuit of the patient in the same way as the prior mechanical vaporizers. Namely, mechanical vaporizers can be removed and replaced with the disclosed close-loop-controlled electronic systems. In certain embodiments, the electronic vaporizer system may be shaped and sized similarly as the mechanical system such that it can fit onto the housing of the anesthesia system at the same location and/or by the same connection means as the mechanical ventilator being replaced.

The electronic vaporizer system is configured to receive a measured end tidal concentration of the anesthetic agent being delivered by the vaporizer and compare the measured end tidal concentration to a desired end tidal concentration to be maintained for the patient. For example, desired end tidal concentration may be, for example, a minimum alveolar concentration (MAC) value and may also include end tidal $CO_2$ and/or $O_2$. The desired end tidal concentration may be set by the clinician or may be automatically set and controlled by the electronic vaporizer system, such as according to a predetermined routine. The electronic vaporizer system automatically delivers an amount of vaporized agent to the patient based on the comparison of the measured end tidal concentration to the desired end tidal concentration. For example, the electronic vaporizers system may determine a change in the amount of vaporized agent to be delivered to the patient breathing circuit based on a difference between the measured end tidal concentration and a desired end tidal concentration, and to control the vaporizer to effectuate the change in order to maintain the measured end tidal concentration within a predetermined range of the desired end tidal concentration In certain embodiments, the electronic vaporizer system may include and/or be communicatively connected to a depth of anesthesia monitor, such as BIS monitor or a train-of-four monitor configured to measure a depth of anesthesia of the patient. The electronic vaporizer system may be configured to utilize the depth of anesthesia information to provide further closed-loop-control in order to maintain the patient at a desired depth of anesthesia. For example, the electronic vaporizer system may be configured to set a desired end tidal concentration, or determine a change in the desired end tidal concentration, in order to achieve or maintain the desired depth of anesthesia. The system then controls delivery of vaporized agent based on that set desired end tidal concentration, using the measured end tidal concentration as feedback.

The system may further be configured to receive and/or follow one or more concentration routines providing end tidal concentration values over time, and to automatically adjust the desired end tidal concentration over time according to the concentration routine. The system may further be configured to calculate a recommended anesthesia concentration based on patient demographic data, for example, and to advise the clinician of the recommendation and/or to automatically adjust the desired end tidal concentration based on the recommended concentration. Thereby, transition periods of anesthetic delivery, such as induction and emergence, can be automatically controlled to maintain the patient's end tidal concentration at predefined desired levels over time. The provides safe and precise control of anesthetic during critical periods and frees the clinician to focus on other areas of patient care.

Figure 2:
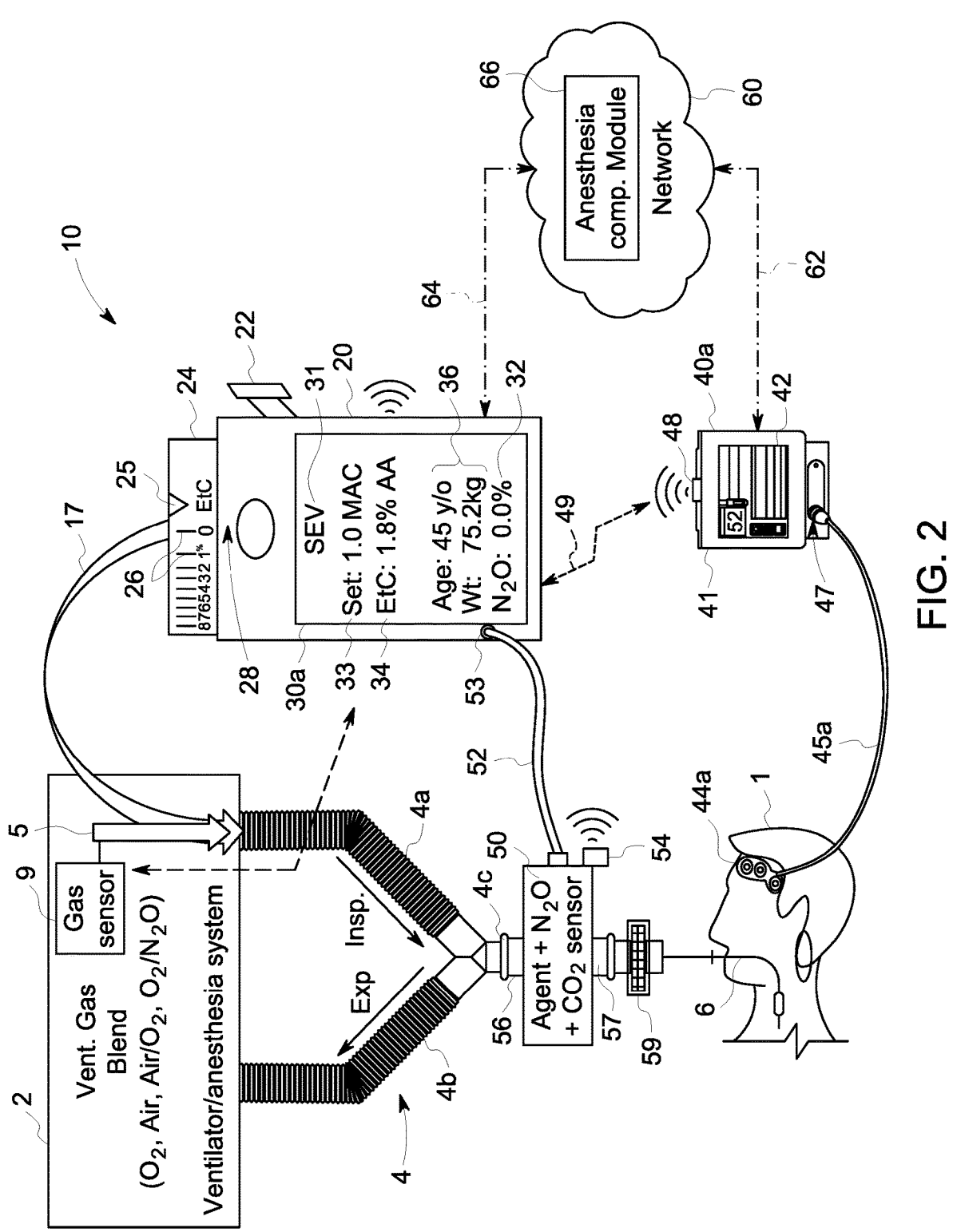
FIG. 2 depicts another embodiment of an electronic vaporizer system connected to a ventilator system for delivering anesthesia to a patient.

FIGS. 1 and 2 depict embodiments of an electronic vaporizer system 10 operably connected to a ventilator system 2 and configured to deliver vaporized anesthetic agent to a patient breathing circuit 4. The electronic vaporizer system 10 includes an electronic vaporizer 12 and one or more sensors communicatively connected thereto, including a gas sensor 50 configured to measure end tidal concentration of the anesthetic agent in exhalation gasses from patient and one or more physiological sensors 44 configured to measure physiological signals related to, or indicating, a depth of anesthesia of the patient 1. The electronic vaporizer 12 is configured to receive the measured end tidal concentration of the anesthetic agent and/or the depth of anesthesia of the patient determined based on the physiological signals and to radically control delivery of vaporized agent to the patient accordingly.

The electronic vaporizer 12 includes a sump 16, or reservoir, containing anesthetic agent to be delivered to the patient, such as Sevoflurane, Desflurane, Enflurane, etc. The sump 16 is configured to be refillable, such as from a refill bottle, as is standard in the relevant art. Thus, the sump 16 has sufficient volume capacity such that it can receive at least the entire volume of a standard refill container. In one embodiment, the sump can accommodate up to about 300 mL of liquid agent. The electronic vaporizer 12 includes a vaporizer unit 14 that vaporizes liquid anesthetic agent housed in a sump 16 and delivers the vaporized agent to the patient breathing circuit 4. For example, the breathing circuit 4 may include a circle breathings system 3, and the vaporizer unit 14 may be configured to deliver vaporized agent such that inhalation gasses comprises anesthetic agent are injected into the circle breathing system 3 and delivered to the patient by the ventilator system 2.

The electronic vaporizer 12 further includes a controller 18 configured to control the vaporizer unit to deliver an amount of vaporized agent to maintain a desired end tidal concentration for the patient 1. The control system for the electronic vaporizer system includes the controller 18 for the vaporizer unit 14 and may also include other control devices communicatively connected to the controller 18. For example, the controller 18 may act in concert with an anesthesia computation module 66 on a network 60 communicatively connected to the electronic vaporizer 12 and/or a controller associated with a depth of anesthesia monitor 40, such as a BIS monitor 40a, and/or a controller 8 for the ventilator system 2.

A gas sensor, which may be a set of sensors, is positioned to measure end tidal concentration of anesthetic agent and other gasses in exhalation gasses within the patient breathing circuit 4. The patient breathing circuit 4 includes an inspiratory section 4a that carries inhalation gasses from the ventilator system to the patient interface 6. The expiratory section is configured to carry exhalation gasses from the patient back to the ventilator 2. The patient interface is commonly, for example, an endotracheal tube as illustrated in FIG. 2. In other embodiments, the patient interface 6 may be a facial mask or some other device configured to create a sealed interface between the patient's airway and the breathing circuit 4. In the depicted example, the gas sensor 50 is positioned between the patient interface 6 and the inspiratory and expiratory arms of the patient breathing circuit 4. Humidity and moisture exchange filter 59 may be positioned between the patient interface 6 and the gas sensor 50 in order to remove moisture from the exhalation gasses prior to measurement.

The gas sensor is configured to measure concentration of the anesthetic agent in the exhalation gasses from the patient, and may also be configured to measure a concentration of nitrous oxide ($N_2O$) and carbon dioxide ($CO_2$) and oxygen ($O_2$). Such concentration measurements are taken during the exhalation cycle where exhalation gasses exit the patient's lungs through the patient interface 6 through the filter 59 to the first connector end 57 of the unit containing the gas sensor 50 and out the second connector end 56, which is connected to the connector end 4c of the patient breathing circuit hose. The gas sensor 50 may further be configured to measure flowrate, including inspiratory flow rate and expiratory flow rate, as well as other gas concentration measurements, which may be inspiratory or expiratory measurements.

The concentration and other measurements from the gas sensor 50 are communicated to the electronic vaporizer 12, which may be by a physical data connection and/or by wireless means. In the example at FIG. 2, the gas sensor 50 is connected by cable 52 to the receiver port 53 on the electronic vaporizer 12. The gas sensor 50 also includes a wireless transmitter 54, which may be a wireless transceiver 42a communication, which is configured to wirelessly broadcast the concentration and other measurements conducted by the gas sensor 50. Such wireless communications may be received by the network 60 such as the computer network system for the operating ward and/or by the hospital or healthcare facility network. In certain embodiments, the concentration and/or other gas measurement may also be received at the depth of anesthesia monitor 40. In certain embodiments, the physical connection between the gas sensor 50 and the electronic vaporizer 12 may be eliminated and the electronic vaporizer 12 may be configured to receive wireless transmission of the measurements from the gas sensor 50.

An additional gas sensor 9 may be configured to measures input gas from the ventilator to the patient's breathing circuit and configured to measure the ventilation gas blend provided by the ventilator 2. Such a gas sensor 9 may be positioned upstream of the delivery point from the vaporized agent and may be configured to measure flowrate and gas concentrations of the ventilator gas blend such as measurement of oxygen ($O_2$) and $N_2O$ in the ventilator gas blend. This provides information regarding the input gasses and flow rates provided by the ventilator system. In certain embodiments, the gas sensor 9 may be incorporated in the ventilator system 2 and the gas measurements may be communicated by the ventilator system 2 to the electronic vaporizer 12. In other embodiments, the gas sensor 9 may be a stand-alone sensor connected at a point in the breathing circuit and configured to communicate directly with the electronic vaporizer 12, which may be by wired or wireless means as described above. The input gas concentration information may also be supplied by an electronic gas mixer built into the anesthesia machine, if so equipped. For example, the additional gas sensor 9 may be integrated into an electronic gas mixer that automatically blends and delivers mixed gas to the patient breathing circuit (N2O/O2, Air/O2, O2 or Air). In such an embodiment, the gas composition is obtained from the electronic gas mixer through communications with therewith, which can be wired or wireless communications as described herein.

The system 10 may further include a depth of anesthesia monitor 40 configured to measure a depth of anesthesia of the patient. Various depths of anesthesia monitors are well known in the relevant art, including bispectral index (BIS) monitors, train-of-four monitors, facial twitch monitors, and others. In the example at FIG. 2, the depth of anesthesia monitor 40 is a BIS monitor 40a. The BIS monitor includes a physiological sensor 44 in the form of a strip of EEG electrodes 44a configured to be placed on the forehead of the patient 1 and to measure EEG activity from the patient. The BIS monitor 40a is configured to determine a depth of anesthesia, or a hypnotic level, of the patient.

In the example at FIG. 2, the BIS monitor 40a is a stand-alone device having a housing 41 to which the EEG electrode patch 44a is connected by a cable 45a to a receiver port 47 on the housing 41. The BIS monitor includes a user interface display 42 configured to display the depth of anesthesia and EEG information collected by the monitor. The system 10 is configured such that the depth of anesthesia information gathered by the BIS monitor 40a is communicated to the electronic vaporizer 12. In certain embodiments, the BIS monitor 40a includes a wireless transmitter or transceiver 48 configured to wirelessly communicate the depth of anesthesia and/or EEG information. The wireless transmission may be received at the electronic vaporizer 12.

For example, a wireless communication link 49 may be established between the electronic vaporizer 12 and the BIS monitor 40a, i.e., between the I/O communication transceiver 19 and the transceiver 48, for communication of the depth of anesthesia information. Such communication may be by any wireless communication protocol, such as Bluetooth, Bluetooth Low Energy (BLE), ANT, and ZigBee. Alternatively, the wireless transceivers of the BIS 40a and the electronic vaporizer 12 may communicate with one another via a longer-range wireless system, such as on a network operating on the wireless medical telemetry service (WMTS) spectrum or on a WiFi-compliant wireless local area network (WLAN). In other embodiments, the BIS 40a and the electronic vaporizer 12 may be body area network (BAN) devices, such as medical body area network (MBAN) devices, that operate as a wireless network of wearable or portable computing devices.

Alternatively or additionally, the electronic vaporizer system 10 may be configured to communicate with and receive communications from a hospital computer network, which may be wireless or wired communication means. The network 60 may include an anesthesia computation module 66 executable to communicate with the electronic vaporizer 12 and to oversee the anesthetic delivery routines and instructions being executed by the system. The system 10 may be configured such that the depth of anesthesia information is also received at the hospital network 60 and may be communicated from the network 60 to the electronic vaporizer 12. In the example at FIG. 2, the electronic vaporizer 12 communicates with the network 60 via wireless link 64 and the BIS monitor communicates with the network 60 via wireless link 62. For example, the network 60 may be a local area network for the hospital or for the operating area of the hospital or other medical facility.

In one arrangement, the electronic vaporizer 12 and/or the BIS 40a may be configured as edge devices operating in an edge computing system where a central computer system for the operating department of the healthcare facility, for example, collects and analyzes patient data and ventilation data in order to oversee and guide the end tidal delivery of anesthetic agent to the patient. For example, the electronic vaporizer 12, depth of anesthesia monitor 40, and gas sensor 50 may all be edge devices communicating information to and receiving information from one or more edge servers comprising part of the network 60.

In other embodiments, the BIS monitor 40a or other depth of anesthesia monitor 40 may be incorporated within a housing 20 of the electronic vaporizer 12. As shown in FIG. 1, the depth of anesthesia monitor 40 may be integrated with controller 18, or integrally housed with the vaporizer unit 14, sump 16, and other elements of the electronic vaporizer 12. In such an embodiment, the physiological sensor 44, such as the EEG patch 44a or a train-of-four sensor, is connected by communication link 45 to the housing 20 of the electronic vaporizer 12. The communication link 45 may be by wired or wireless means, examples of which are described above. In such an embodiment, the depth of anesthesia monitor 40 may include a dedicated controller for calculating the depth of anesthesia values. In other embodiments, the controller 18 may be configured to calculate the depth of anesthesia values based on the physiological data gathered and filtered by the depth of anesthesia monitor electronics.

The housing 20 of the vaporizer system 12 may be configured to removably attach to the ventilator system 2. For example, the housing 20 may be configured to connect to existing ventilator systems 2 in place of an existing manual vaporizer. Thus, the housing 20 may be shaped similar to the manual vaporizer systems that it is configured to replace, or at least a portion of the housing that connects to the ventilator system 2 may be shaped and configured similarly or identically to the existing manual vaporizer housing. Thereby, the disclosed electronic vaporizer system 10 can replace the existing manual vaporizers on a wide variety of installed ventilator systems 2.

The housing 20 may include a refill port 22 configured to receive a refill container of anesthetic agent in order to refill the sump 16. A dial 24 may also be provided on the housing 20. The dial 24 may be configured to control a mode of the vaporizer system, where the dial 24 is movable between a position associated with a manual mode, where a clinician manually controls the amount of vaporized agent delivered to the patient breathing circuit, and an automatic mode, where the control system automatically controls vaporizer unit 14 to deliver the amount of vaporized agent to maintain a certain end tidal concentration anesthetic agent for the patient. In the example depicted at FIG. 2, the automatic mode position 25 is at a far end of the rotational range of the dial 24. When the dial 24 is in that maximum rotational position, the automatic mode marker 25 is aligned with the selection marker 28 on the housing 20. When the dial is rotated away from the automatic mode position 25, a manual mode is engaged where the clinician can operate the dial to select an end tidal concentration. Various position indicators 26 are associated with respective concentration outputs and the vaporizer unit 14 is controlled accordingly, similarly to existing manual vaporizer controls on manual vaporizer systems. Thus, the depicted electronic vaporizer 10 is also configured to be operated as a manual vaporizer when the automatic mode, or end tidal concentration control mode, is not selected.

In other embodiments, the dial 24 may instead be replaced with another user interface device for engaging and disengaging the automatic mode, such as a switch or a button configured to turn on and off the automatic mode where the control system automatically controls the vaporizer unit to maintain an end tidal concentration of the patient. In still other embodiments, the automatic mode may be engaged through a user interface 30 associated with the electronic vaporizer 12. The user interface 30 may be a standalone device, such as a touchscreen that is separately housed from the housing 20 of the electronic vaporizer, as illustrated in FIG. 1. In other embodiments, such as that illustrated in FIG. 2, the user interface 30a may be integrated into the housing 20 of the electronic vaporizer 12. The integrated interface 30a may be a touchscreen, such as an LCD touchscreen on a front side of the housing 20 that faces the clinician.

The user interface 30, 30a is configured to display information relating to anesthetic delivery and control, such as including an agent indicator 31 indicating the anesthetic agent being delivered by the electronic vaporizer 12, a desired concentration indicator 33 displaying the desired end tidal concentration setting which is to be automatically maintained by the system 10, and a measured concentration indicator 34 indicating the current measured end tidal concentration of the anesthetic agent for the patient 1. In the depicted embodiment, the desired concentration indicator 33 presents the desired concentration setting as a minimum alveolar concentration (MAC) value, and the measured concentration indicator 34 presents the measured concentration as a percent by volume of agent in the patient's exhalation gasses. In other embodiments, the measured concentration indicator 34 may be presented as a MAC value and/or the desired concentration indicator may be presented as a percentage by volume value. The user interface may also display an $N_2O$ indicator indicating the end tidal concentration of $N_2O$. Alternatively or additionally, the user interface may also display an inspiratory $N_2O$ concentration, such as measured in the ventilator gas blend by the gas sensor 9 or ventilator electronic gas mixer. The user interface may further include one or more patient demographic indicators 36 providing demographic information about the patient 1, such as age, weight, gender, etc.

The user interface 30, 30a may also be configured to display information, suggestions, and instructions to the clinician. For example, the display may be configured to provide a recommended concentration to the clinician based on patient demographic data and/or a suggestion or instruction to the clinician to adjust the desired end tidal concentration based on the recommended concentration. Alternatively or additionally, the user interface 30, 30a may be configured to prompt a clinician to input and/or receive clinician inputs instructing a desired end tidal concentration and/or inputting one or more concentration routines to be executed by the vaporizer system 12 over time. For example, the clinician may instruct a series of desired end tidal concentrations over a period of time to be executed at a particular stage in a procedure, such as an induction routine for inducing a desired depth of anesthesia, or hypnotic state, of the patient and/or an emergence routine for reducing the patient's depth of anesthesia at a desired rate.

Figure 3:
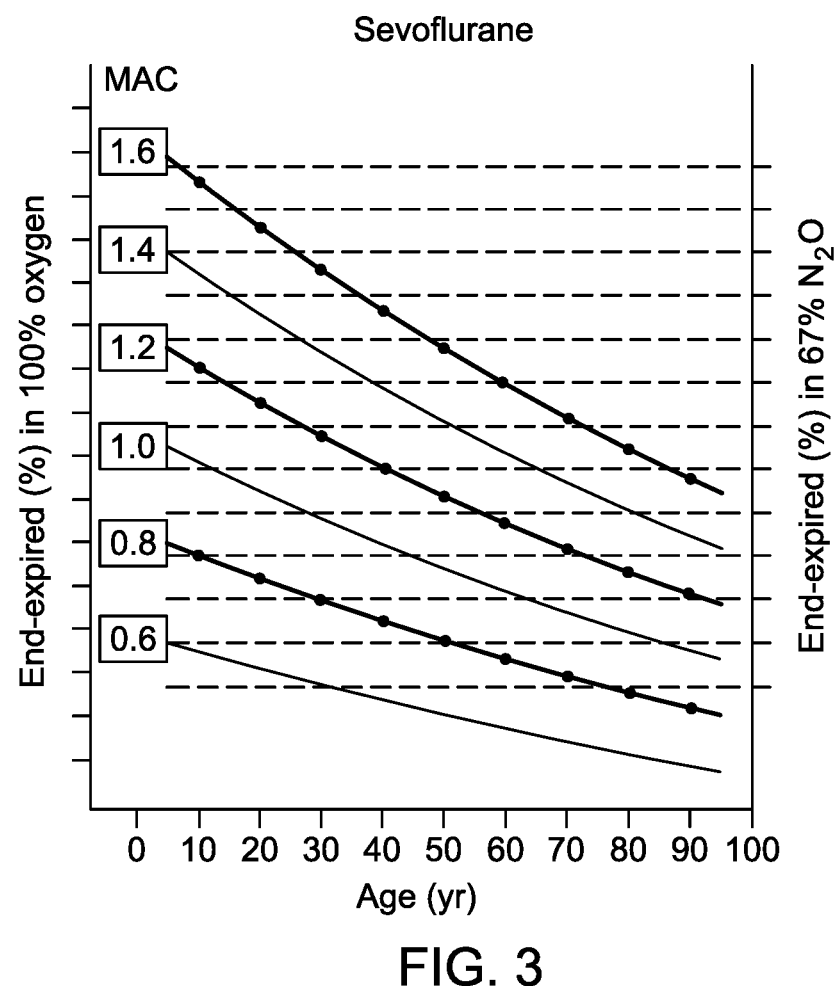
FIG. 3 depicts an exemplary table utilized for calculating a recommended end tidal concentration of Sevoflurane, an exemplary anesthetic agent, based on patient demographic data and other information.

In certain embodiments, the anesthesia computation module 66 may further be configured to calculate recommended concentration values and/or recommended concentration routines for controlling the electronic vaporizer 12 based on patient demographic data and/or historical data for the patient and to provide such recommended concentration values or recommended concentration routines to the electronic vaporizer 12. The anesthesia computation module 66 may be configured to utilize the most up to date anesthetic calculation algorithms and information, including published MAC charts, as well as patient demographic information, medical history, etc. obtained from the patient's medical record, in order to calculate and suggest appropriate end tidal concentration settings and/or routines to provide optimal anesthesia delivery for the patient. An exemplary MAC chart is illustrated at FIG. 3, which provides a desired MAC setting based on expired oxygen, expired $N_2O$, and patient age. In an edge computing system, such MAC charts and other information for computing recommended concentrations for desired end tidal settings can be easily updated implemented at the network level and take advantage of advances in Artificial Intelligence (AI).

Figure 4:
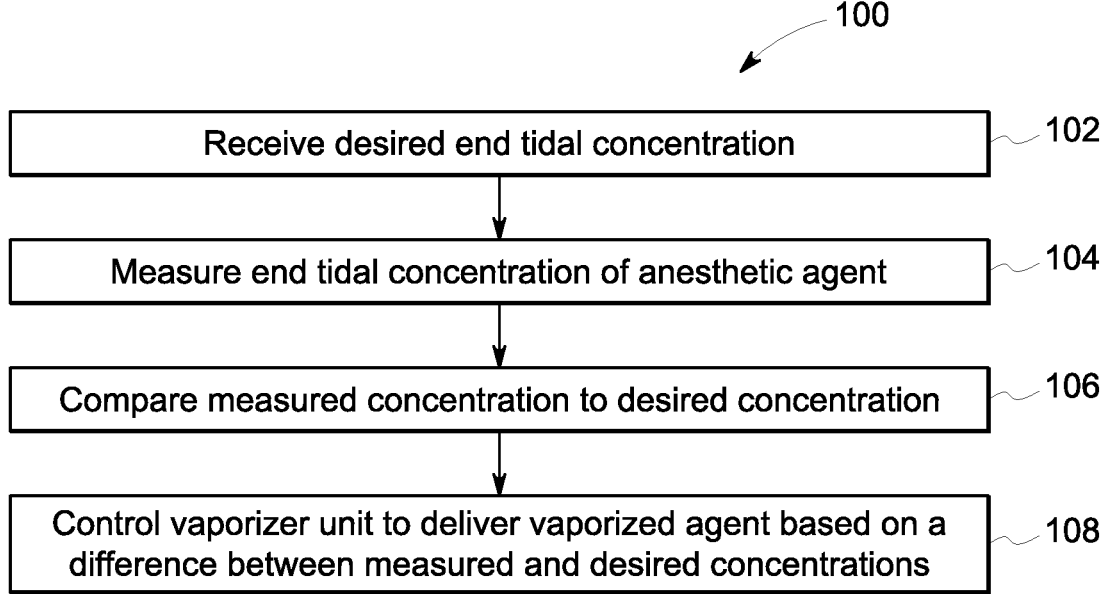
FIGS. 4-6 depict methods, or portions thereof, of controlling electronic vaporizer systems for anesthetic delivery to a patient.
Figure 5:
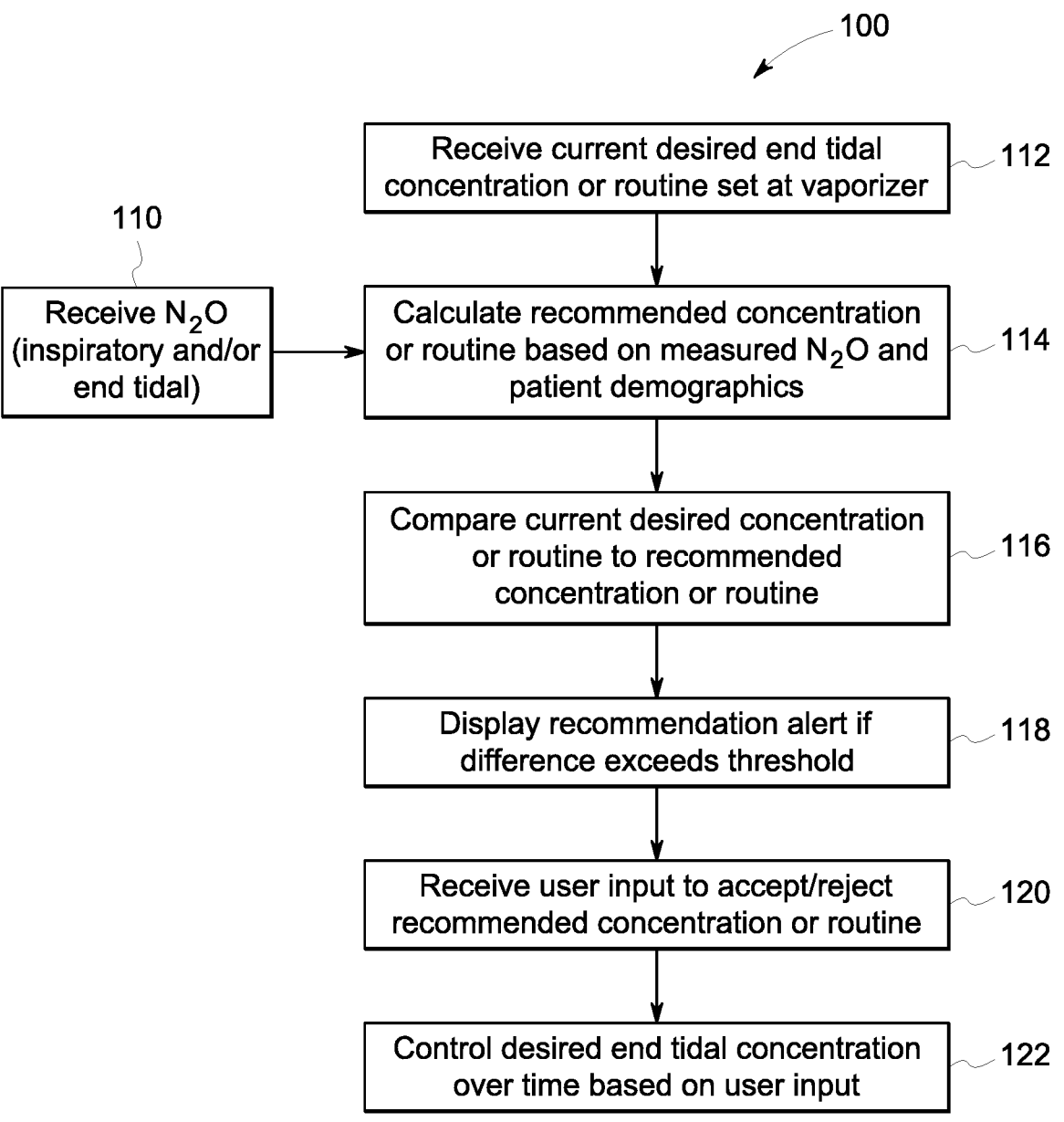
Figure 6:
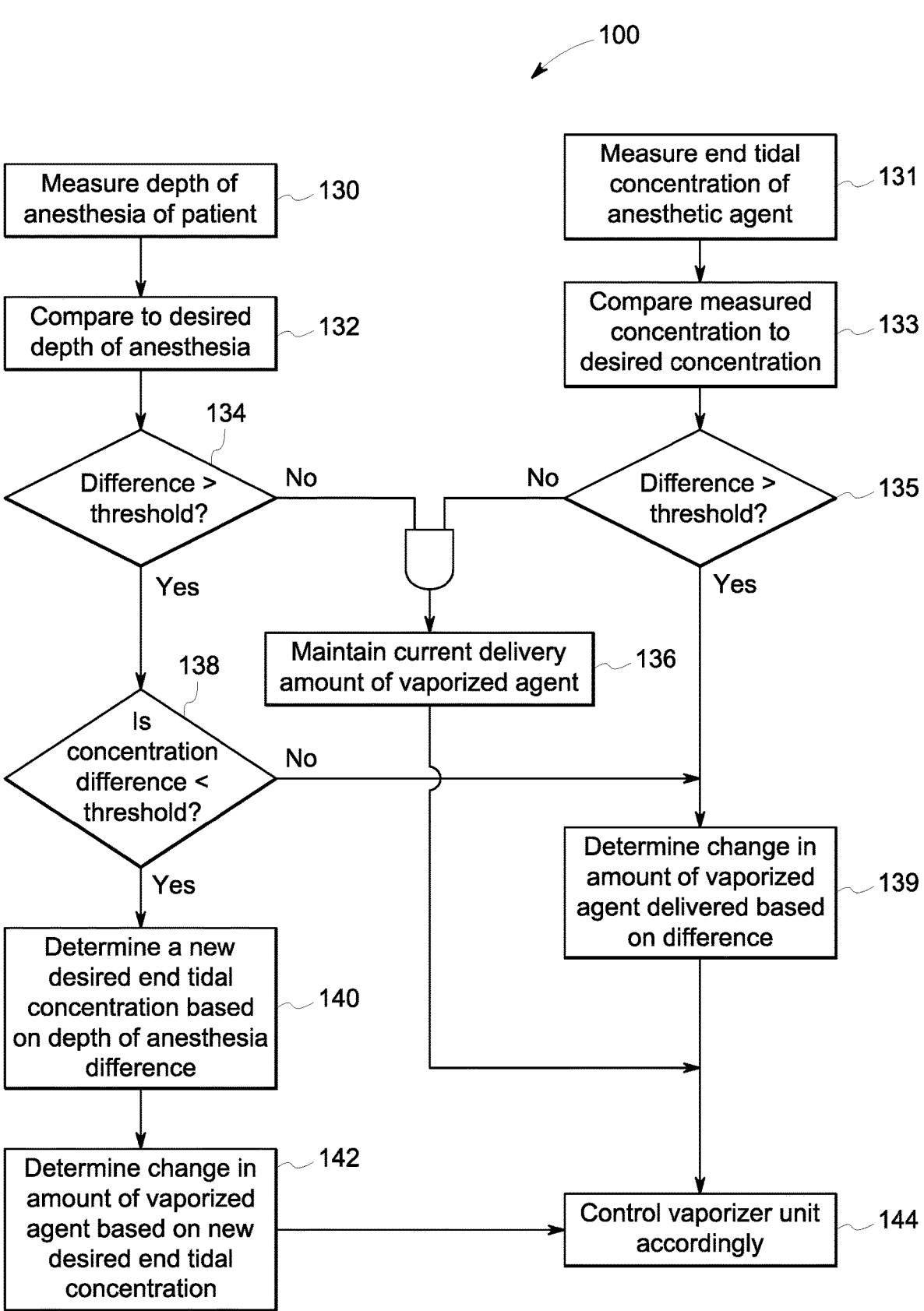

FIGS. 4-6 depict exemplary methods, or portions thereof, of controlling an electronic vaporizer system. In the flowchart at FIG. 4, the method 100 of controlling an electronic vaporizer system includes receiving a desired end tidal concentration at step 102. For example, the desired end tidal concentration may be inputted by a clinician, such as via the user interface 30, or may be automatically determined by the system, such as at the hospital LAN network and instructed by the anesthesia computation module 66. The end tidal concentration of anesthetic agent in exhaled gasses from the patient is measured at step 104, such as by gas sensor 50. The measured concentration is compared to the desired concentration at step 106. The vaporizer unit 14 is then controlled to deliver vaporized agent at step 108 based on the difference between the measured end tidal concentration and the desired end tidal concentration.

FIG. 5 depicts a portion of a control method of a vaporizer system relating to calculation and implementation of recommended concentration values or recommended concentration routines. The recommendation calculations may be carried at the network level, as described above, or the controller 18 of the electronic vaporizer 12 may be configured to conduct the recommendation calculations. Information regarding the inhalation gas being delivered to the patient and the current settings for the electronic vaporizer are provided and utilized to calculate recommended concentrations or routines, which may then be provided as recommendations to a clinician, who may accept or reject the recommendations. Alternatively, such recommendations may automatically be implemented by the electronic vaporizer 12.

In the example shown at FIG. 5, N$_2$O concentration is received at step 110, which may include the inspiratory N$_2$O concentration provided by the ventilator 2, the ventilator gas blend and/or may include the end tidal N$_2$O concentration measured by the gas sensor 50. The current desired end tidal concentration set for the vaporizer, and/or the current concentration routine set for the vaporizer, is received at step 112. A recommended concentration for the end tidal concentration or a recommended concentration routine is calculated at step 114 on the measured N$_2$O value and patient demographics, such as patient age and weight. The current setting, including the end tidal concentration and/or the concentration routine is then compared to the recommended concentration or recommended concentration routine at step 116 to determine if there is a discrepancy between the current vaporizer settings and the recommended values. A recommendation alert is displayed at step 118 if the difference exceeds a threshold difference warranting a change in the vaporizer settings as to improve anesthesia administration to the patient. For example, the recommendation alert may be presented on the user interface 30, 30*a* of the electronic vaporizer 12.

User input is then received at step 120, such as via the user interface 30, 30*a* to accept or reject the recommended concentration or recommended concentration routine. The vaporizer settings are then maintained or adjusted according to the user input so as to control the desired end tidal concentration of anesthetic agent over time for the patient based on the user's acceptance or rejection of the recommendation.

FIG. 6 depicts another embodiment of a method 100 of controlling the electronic vaporizer system 10. A depth of anesthesia of the patient is measured at step 130, such as by a depth of anesthesia monitor 40, 40*a*. The measured depth of anesthesia of the patient is compared to a desired depth of anesthesia of the patient at step 132. At step 134, the control system determines whether the difference between the desired depth of anesthesia and the measured depth of anesthesia exceeds a threshold.

The end tidal concentration of anesthetic agent is measured at step 131 and the measured end tidal concentration is compared to a desired end tidal concentration at step 133. If the difference between the measured and desired end tidal concentration exceeds a threshold value at step 135, then a change in amount of vaporized agent delivered to the patient is determined at step 139 based on the difference.

If, however, the measured and desired depth of anesthesia are within the predefined threshold of one another and the measured and desired end tidal concentration are within the predefined threshold of one another, then the current delivery amount of vaporized agent is maintained, as represented at step 136. In other words, if both the patient's depth of anesthesia and the patient's end tidal concentration are within a predetermined range of the desired values set for the vaporizer, then the current delivery amount is maintained. Otherwise, changes to anesthetic delivery by the electronic vaporizer 12 are effectuated.

Changes in anesthetic delivery amount may be calculated variously based on differences between the measured and desired depth of anesthesia levels and the measured and desired end tidal concentration values. In the depicted example, if the measured end tidal concentration is not within the threshold range of the desired end tidal concentration, then the difference between the measured and desired depth of anesthesia measurements may be attributable to the discrepancy in the end tidal concentration, especially if the discrepancies between the depth of anesthesia values and the end tidal concentration values are consistent. This example assumes such consistency. If the difference between the measured and desired end tidal concentration is greater than the threshold value, then the system adjusts the vaporize agent delivered to the patient based on the difference at step 139 in order to bring the measured end tidal concentration in line with the desired end tidal concentration. In a further embodiment, if the system is unable to achieve the set target end tidal concentration, i.e., the measured end tidal concentration is lower than the desired end tidal concentration, then the system may generate an alarm that it is unable to achieve its programmed target, potentially signaling a failure of the system, leaks in the breathing system, etc.

This is also likely to decrease the difference between the measured depth of anesthesia value and the desired depth of anesthesia value. However, if the difference between the measured and desired end tidal concentration is less than the threshold at step 138, meaning that the measured and desired end tidal concentrations are within a predefined threshold range of one another, then steps may be taken to adjust or recalculate the desired end tidal concentration in order to bring the depth of anesthesia for the patient to the desired depth.

A new desired end tidal concentration is determined at step 140 based on the difference between the measured and desired depth of anesthesia values. A change in the amount of vaporized agent is then determined at step 142 based on the new desired end tidal concentration. The vaporizer unit 14 is then controlled accordingly to deliver the amount of vaporized agent.

As used herein, the terms controller or module may refer to, be part of, or include an application-specific integrated circuit (ASIC), an electronic circuit, a combinational logic circuit, a field programmable gate array (FPGA), a processor (shared, dedicated, or group) that executes code, or other suitable components that provide the described functionality, or a combination of some or all of the above, such as in a system-on-chip. The terms controller or module may include memory (shared, dedicated, or group) that stores code executed by the processor. The term code, as used herein, may include software, firmware, and/or microcode, and may refer to programs, routines, functions, classes, and/or objects. The term shared, as used above, means that some or all code from multiple modules may be executed using a single (shared) processor. In addition, some or all code to be executed by multiple different processors may be stored by a single (shared) memory. The term group, as used above, means that some or all code comprising part of a single controller or module may be executed using a group of processors. Likewise, some or all code comprising a single controller or module may be stored using a group of memories.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

We claim:

1. An electronic vaporizer system comprising:
an anesthetic sump containing anesthetic agent;
a vaporizer unit that vaporizes the anesthetic agent from the sump and delivers the vaporized agent to a patient breathing circuit;
a gas sensor configured to measure end tidal concentration of the anesthetic agent in exhalation gases from a patient;
a control system configured to:
receive the measured end tidal concentration of the anesthetic agent;
compare the measured end tidal concentration to a desired end tidal concentration to be maintained for the patient; and
automatically control the vaporizer unit to deliver an amount of vaporized agent to the patient breathing circuit based on the comparison.

2. The system of claim 1, further comprising at least one ventilation gas sensor configured to sense a flow rate of inhalation gases in the breathing circuit;
wherein the control system is further configured to control the vaporizer unit to deliver the amount of vaporized agent to the patient breathing circuit based on the flow rate of the inhalation gases.

3. The system of claim 1, wherein the control system is configured to determine a change in the amount of vaporized agent to be delivered to the patient breathing circuit based on a difference between the measured end tidal concentration and a desired end tidal concentration, and to control the vaporizer to effectuate the change.

4. The system of claim 1, further comprising a depth of anesthesia monitor configured to measure a depth of anesthesia of the patient;
wherein the control system is further configured to:
determine that a difference between the measured depth of anesthesia and a desired depth of anesthesia exceeds a threshold; and
determine a new desired end tidal concentration based on a difference between the measured depth of anesthesia and a desired depth of anesthesia.

5. The system of claim 1, wherein the control system is configured to receive the desired end tidal concentration as a clinician input via a user interface on the vaporizer system.

6. The system of claim 1, wherein the sump and the vaporizer unit are contained together in a housing.

7. The system of claim 6, further comprising touch screen on the housing configured to receive control inputs for the vaporizer system and to display at least one of the measured end tidal concentration, the desired end tidal concentration, and a difference between the measured end tidal concentration and the desired end tidal concentration.

8. The system of claim 6, wherein the housing is configured to be removably attached to a ventilator system configured to ventilate the patient.

9. The system of claim 6, further comprising a depth of anesthesia monitor configured to connect to a sensor and measure a depth of anesthesia of the patient, wherein the depth of anesthesia monitor is housed within the housing.

10. The system of claim 6, further comprising a dial on the housing movable to control a mode of the vaporizer system between a manual mode where a clinician manually controls the amount of vaporized agent delivered to the patient breathing circuit and an automatic mode where the control system automatically controls the vaporizer unit to deliver the amount of vaporized agent to the patient breathing circuit.

11. The system of claim 1, wherein the control system is further configured to:
receive one or more concentration routines; and
automatically adjust the desired end tidal concentration according to the concentration routine.

12. The system of claim 1, wherein the control system is further configured to:
calculate a recommended concentration based on patient demographic data and to adjust the desired end tidal concentration based on the recommended concentration.

13. A method of controlling a vaporizer system configured to vaporize an anesthetic agent and deliver the vaporized agent to a patient breathing circuit, the method comprising:
measuring end tidal concentration of the anesthetic agent in exhalation gases from a patient;
comparing the measured end tidal concentration to a desired end tidal concentration to be maintained for the patient; and
automatically controlling a vaporizer unit to deliver an amount of vaporized agent to the patient breathing circuit based on the comparison so as to maintain the measured end tidal concentration within a predetermined range of the desired end tidal concentration.

14. The method of claim 13, further comprising sensing a flow rate of the inhalation gases in the breathing circuit; and
controlling the vaporizer unit to deliver the amount of vaporized agent to the patient breathing circuit based further on the flow rate of the inhalation gases.

15. The method of claim 13, further comprising determining a change in the amount of vaporized agent to be delivered to the patient breathing circuit based on a difference between the measured end tidal concentration and a desired end tidal concentration, and controlling the vaporizer unit to effectuate the change.

16. The method of claim 13, further comprising measuring a depth of anesthesia of the patient;
determining that a difference between the measured depth of anesthesia and a desired depth of anesthesia exceeds a threshold; and determining a new desired end tidal concentration based on a difference between the measured depth of anesthesia and a desired depth of anesthesia.

17. The method of claim 13, further comprising sensing a dial position of a dial on the vaporizer system associated with an automatic mode prior to automatically controlling the vaporizer unit to deliver the amount of vaporized agent to the patient breathing circuit.

18. The method of claim 13, further comprising:

receiving one or more concentration routines selected by a clinician; and automatically adjusting the desired end tidal concentration according to the selected concentration routine.

19. The method of claim 13, further comprising:

sensing $N_2O$ concentration of the inhalation gases in the breathing circuit; and determining the desired end tidal concentration based on the $N_2O$ concentration.

20. The method of claim 13, further comprising:

receiving a recommended concentration from a network computer calculated based on patient demographic data for the patient;

comparing the desired end tidal concentration to the recommended concentration;

determining a concentration change recommendation based on the comparison; and displaying, on a display of the vaporizer system, the concentration change recommendation.

21. The method of claim 20, further comprising automatically adjusting the desired end tidal concentration based on the recommended concentration.

* * * * *